Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful

8 PT.

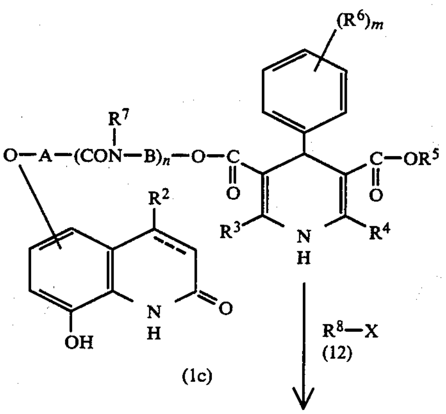

(1c)

(12)

6 PT.

Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful $$v'_{ref}(t) = K\, r\, \delta \left( t - \frac{2L - 2d_s}{v_w} \right) + K\,(1 - r^2)e^{-2\alpha s d s}$$

4 PT.

Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful $$\cos \beta^* = \frac{K_2 - n\frac{T'}{v''}}{\sqrt{K_1^2 + \left(K_2 - n\frac{T'}{v''}\right)^2 + K_3^2}}$$

$$(K_1x+K_2y+K_3z+T)+n(K''_1x+K'{}'_2y+K''_3z+T'')=0$$

8 PT.

are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful

6 PT.

Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful

4 PT.

Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful

| $r_1$ ($L_1$) | $r_6$ ($L_3$) | $r_7$ ($L_4$) |
|---|---|---|
| K = 1.0 | K = 1.0 | K = 0.0 |
| $C_2$ = 0.0 | $C_2$ = 0.0 | $C_2$ = 0.0 |
| $C_4 = -0.15691 \times 10^{-6}$ | $C_4 = +0.95381 \times 10^{-7}$ | $C_4 = -0.22891 \times 10^{-5}$ |
| $C_6 = -0.40068 \times 10^{-10}$ | $C_6 = -0.73871 \times 10^{-10}$ | $C_6 = +0.12283 \times 10^{-9}$ |
| $C_8 = +0.21016 \times 10^{-13}$ | $C_8 = +0.12280 \times 10^{-13}$ | $C_8 = +0.84230 \times 10^{-13}$ |
| $C_{10} = -0.37685 \times 10^{-17}$ | $C_{10} = -0.33177 \times 10^{-17}$ | $C_{10} = -0.20592 \times 10^{-16}$ |

$f_1$ = 314.6
$f_2$ = 88.0
$f_3$ = −481.2
$f_4$ = −99.6

100mm

= 101.2 Aperture ratio: 1:1.10
agnification of projection: $-7.997^x$
alf angle of view: 28.56°

| | | | |
|---|---|---|---|
| 43.454 | $d_1$ = 11.0 | $n_1$ = 1.49380 | $L_1$ |
| -1542.254 | $d_2$ = 68 | | |
| 16.976 | $d_3$ = 20.0 | $n_2$ = 1.62286 | $L_2$ |
| 10.914 | $d_4$ = 2.87 | | |
| -89.375 | $d_5$ = 5.0 | $n_3$ = 1.59501 | $L_3$ |
| -127.071 | $d_6$ = 58.8 | | |
| -48.609 | $d_7$ = 5 | $n_4$ = 1.49380 | $L_4$ |
| ∞ | $d_8$ = 5 | $n_5$ = 1.45000 | S |
| ∞ | $d_9$ = 8 | $n_6$ = 1.51872 | G |

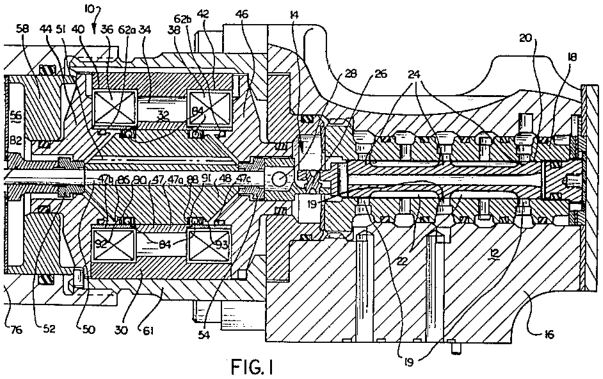

FIG.1

IMAGE SYSTEM
TEST TARGET
A

U.S. DEPARTMENT OF COMMERCE
PATENT AND TRADEMARK OFFICE

PROCESS FOR MAKING S-PHENENYLTRIS(SULFONYLIMINO)TRI-BENZENE MONO- AND DI-SULFONIC ACIDS AND SALTS

CROSS-REFERENCE TO RELATED APPLICATIONS

This application is a divisional of copending application Ser. No. 104,614 filed Dec. 17, 1979, now U.S. Pat. No. 4,265,908, which in turn is a divisional of application Ser. No. 973,313, filed Dec. 26, 1978, now U.S. Pat. No. 4,208,346.

BACKGROUND OF THE INVENTION

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 patients in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in the body processes can be found in, for example, Bull. World Health Org., 39, 935–938 (1968); Ann. Rev. Medicine, 19, 1–24 (168); The Johns Hopkins Med. J., 128, 57–74 (1971); Harvey Lectures, 66, 75–104 (1972); The New England Journal of Medicine, 287, 452–454; 489–495; 545–549; 592–596; 642–646; (1972); Scientific American, 229, (No. 5), 54–66 (1973); Federation Proceedings, 32, 134–137 (1973); Medical World New, Oct. 11, 1974, pp. 53–66; J. Allergy Clin. Immunol., 53, 298–302 (1974); Cold Spring Harbor Conf. Cell Proliferation 2/Proteases Biol. Control/229–241 (1975); Ann. Review of Biochemistry, 44, 697 (1975); Complement in Clinical Medicine, Disease-a-Month, (1975); Complement, *Scope*, Dec. 1975; Annals of Internal Medicine, 84, 580–593 (1976); "Complement: Mechanisms and Functions", Prentice-Hall Englewood Cliffs, N.J. (1976); Essays Med. Biochem. 2, 1–35 (1976); Hospital Practice, 12, 33–43 (1977); Perturbation of Complement in Disease, Chap. 15 in Biological Amplification Systems in Immunology (Ed. Day and Good), Plenum, New York and London (1977); Am. J. Clin. Pathology, 68, 647–659 (1977).

The complement system can be considered to consist of three sub-systems: (1) a recognition unit (C1q) which enables it to combine with antibody molecules that have detected a foreign invader; (2) an activation unit C1r, C1s, C2, C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review of Biochemistry, 38, 389 (1969); Journal of Immunology, 119, 1–8, 1195, 1358–1364, 1482 (1977).

A variety of substances have been disclosed as inhibiting the complement system, i.e., as complement inhibitors. For example, the compounds 3,3′-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, British Journal of Experimental Pathology, 33, 327–339 (1952). German Pat. No. 2,254,893 or South African Pat. No. 727,923 discloses certain 1-(diphenylmethyl)-4-(3-phenylallyl)piperazines useful as complement inhibitors. Other chemical compounds having compelment inhibiting activity are disclosed in, for example, Journal of Medicinal Chemistry, 12, 415–419; 902–905; 1049–1052; 1053–1956 (1969); Canadian Journal of Biochemistry, 47, 547–552 (1969); The Journal of Immunology, 104, 279–288 (1970); The Journal of Immunology, 106, 241–245 (1971); The Journal of Immunology, 111, 1061–1066 (1973); Biochim. Biophys. Acta, 317, 539–548 (1973); Life Sciences, 13, 351–362 (1973); Journal of Immunology, 113, 584 (1974); Immunology, 26, 819–829 (1974); Journal of Medicinal Chemistry, 17, 1160–1167 (1974); Biochim.

8 PT.

Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful

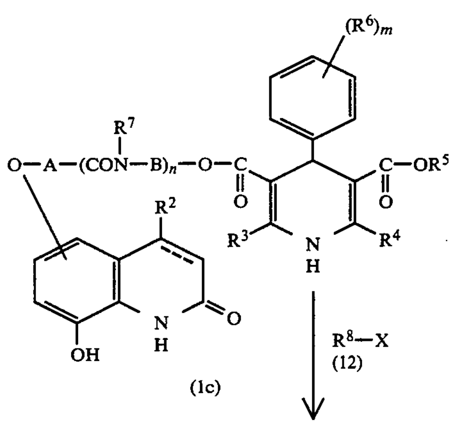

(1c)

6 PT.

Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful $$v'_{refl}(t) = K\, r\, \delta\left(t - \frac{2L - 2d_s}{v_w}\right) + K(1 - r^2)e^{-2\alpha s d s}$$

4 PT.

Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful $$\cos\beta^* = \frac{K_2 - n\frac{T'}{v''}}{\sqrt{K_1^2 + \left(K_2 - n\frac{T'}{v''}\right)^2 + K_3^2}}$$

$$(K_1x+K_2y+K_3z+T)+n(K''_1x+K'_2y+K''_3z+T'')=0$$

8 PT.

are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful

6 PT.

Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful

4 PT.

Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful

| $r_1$ ($L_1$) | $r_6$ ($L_3$) | $r_7$ ($L_4$) |
|---|---|---|
| K = 1.0 | K = 1.0 | K = 0.0 |
| $C_2$ = 0.0 | $C_2$ = 0.0 | $C_2$ = 0.0 |
| $C_4$ = −0.15691 × $10^{-6}$ | $C_4$ = +0.95381 × $10^{-7}$ | $C_4$ = −0.22891 × $10^{-5}$ |
| $C_6$ = −0.40068 × $10^{-10}$ | $C_6$ = −0.73871 × $10^{-10}$ | $C_6$ = +0.12283 × $10^{-9}$ |
| $C_8$ = +0.21016 × $10^{-13}$ | $C_8$ = +0.12280 × $10^{-13}$ | $C_8$ = +0.84230 × $10^{-13}$ |
| $C_{10}$ = −0.37685 × $10^{-17}$ | $C_{10}$ = −0.33177 × $10^{-17}$ | $C_{10}$ = −0.20592 × $10^{-16}$ |

$f_1$ = 314.6
$f_2$ = 88.0
$f_3$ = −481.2
$f_4$ = −99.6

100mm

| | | | |
|---|---|---|---|
| = 101.2 Aperture ratio: | | 1:1.10 | |
| agnification of projection: | | −7.997$^x$ | |
| alf angle of view: | | 28.56° | |
| 43.454 | $d_1$ = 11.0 | $n_1$ = 1.49380 | $L_1$ |
| −1542.254 | $d_2$ = 68 | | |
| 16.976 | $d_3$ = 20.0 | $n_2$ = 1.62286 | $L_2$ |
| 10.914 | $d_4$ = 2.87 | | |
| −89.375 | $d_5$ = 5.0 | $n_3$ = 1.59501 | $L_3$ |
| −127.071 | $d_6$ = 58.8 | | |
| −48.609 | $d_7$ = 5 | $n_4$ = 1.49380 | $L_4$ |
| ∞ | | | |
| ∞ | $d_8$ = 5 | $n_5$ = 1.45000 | S |
| ∞ | $d_9$ = 8 | $n_6$ = 1.51872 | G |

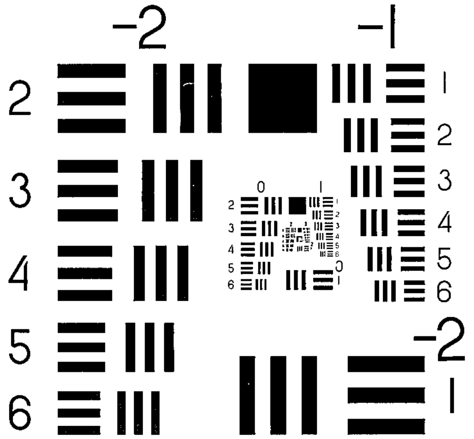

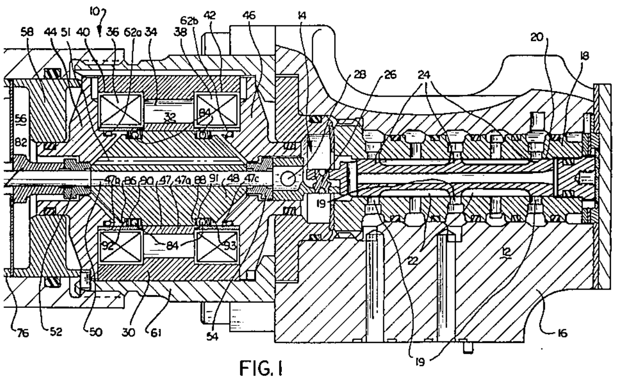

FIG. I

IMAGE SYSTEM
TEST TARGET
A

U.S. DEPARTMENT OF COMMERCE
PATENT AND TRADEMARK OFFICE dium ethoxide in dimethylsulfoxide followed by treatment with acetic acid to give the desired 5,5′,5″-[s-phenenyltris(sulfonylimino)]tri-m-benzenedisulfonic acid, hexasodium salt (7).

Following the procedure outlined above, utilizing sodium p-nitrobenzenesulfonate as a starting material affords the compound, 4,4′,4″-[s-phenenyltris(sulfonylimino)]tri-benzenesulfonic acid, trisodium salt.

Compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The compounds herein may also be used in the therapeutic treatment of warm-blooded animals having non-immunologic diseases such as paroxysmal nocturnal hemoglobinuria, hereditary antioneurotic edema (treated with Suramin, etc.) and inflammatory states induced by the action of bacterial or lysosomal enzymes on the appropriate complement components as for example, inflammation following coronary occlusion. They may also be useful in the treatment of transplant rejection and as blood culture or transport mediums.

The compounds of the present invention may be administered internally, e.g., orally or parenterally, such as intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those or primary amines, e.g., ethylamine; secondary amines, e.g., diethylamine or diethanolamine; tertiary amines, e.g., pyridine or triethylamine or 2-dimethylaminomethyldibenzofuran; aliphatic diamines, e.g., decamethylenediamine; and aromatic diamines, can be prepared. Some of these are soluble in water, others are soluble in saline solution, and still others are soluble and can be used for purposes of preparing suspensions for injection. Furthermore, as well as the sodium salt, those of the alkali metals, such as potassium and lithium; of ammonia; and of the alkaline earth metals, such as calcium or magensium, may be employed. It will be apparent, therefore, that these salts embrace, in general, derivatives of salt-forming cations.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magensium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac, and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonsful, droppersful, ampules, vials, segregated multiples of any of the foregoing and other forms as herein described.

The complement inhibiting activity of the compounds of this invention has been demonstrated by one or more of the following identified tests: (i) Test Code 026 (Cl inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3-C9 inhibitor)—This test determines the ability of the late components of human complement (C3-C9) to lyse EAC 142 in the presence of appropriate dilutions of the test compound. An active inhibitor protects EAC 142 from lysis by human C3-C9; (iii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test—Lethal shock is produced in guinea pigs by an i.v. injection of anti-Forssman antiserum and the harmonic mean death time of treated guinea pigs is compared with that of simultaneous controls; (vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; (viii) Cap 50 Test—Here, appropriate amounts of the test compound are added to a pool of guinea pig serum in vitro, after which the undiluted serum capillary tube assay referred to above is run. The concentration of compound inhibiting 50% is reported; and (viii) Guinea Pig Intraperitoneal Test (GPIP)—Guinea Pigs weighing about 300 g. are dosed intraperitoneally (i.p.) with 200 mg./kg. of the test compound dissolved in saline and adjusted to pH 7-8. Approximately 0.4 ml. blood samples, taken by orbital sinus puncture 30 minutes and 1 hour after injections, are collected directly into centrifuge tubes; 5 ml. blood samples, taken by decapitation 2 hours after injection are collected directly into diSPo® beakers. The samples were allowed to clot, centrifuged, and the resultant sera were assayed for complement activity using the capillary complement assay. Percent inhibition are calculated by comparison with simultaneous controls. The results appear in Table I together with results of Test Code 026, 035, 036 and Cap 50. Table I shows that the principal compound of the invention possesses highly significant in vitro and in vivo complement inhibiting activity in warm-blooded animals.

TABLE I

| Compound | Biological Activities: Cl 026* Wells | C-Late 035* Wells | Shunt Inhibition 036* Wells | Cap 50 | In Vivo Activity (Guinea pig) % Inhibition Intraperitoneal Time (Min.) 30 | 60 | 120 |
|---|---|---|---|---|---|---|---|
| 3,5',5''-[s-Pheneyltris(sulfonylimino)]tri-m-benzenedisulfonic acid hexasodium salt | +8** | N | N | 116 | −75 | −75 | −81 |

*Tests identified by code herein
**Activity in wells, a serial dilution assay; higher well number indicates higher activity. The serial dilutions are two-fold
N = Negative

DETAILED DESCRIPTION OF THE INVENTION

The following examples describe in detail the preparation and formulation of representative compounds of the present invention.

EXAMPLE 1

5,5',5''-[s-Phenenyltris(sulfonylimino)]tri-m-benzenedisulfonic acid, hexasodium salt A mixture of 141 g. of disodium benezene-1,3-disulfonate in 450 ml. of concentrated sulfuric acid is stirred and heated to 65° C. During the course of 3¼ hours, 120 g. of sodium nitrate are added in portions while the mixture is stirred and maintained at 70° C. After addition is complete, the mixture is cooled to 5° C. and 900 g. of ice are added with stirring. The mixture is filtered overnight with vacuum. The cake is warmed on a steam bath in 250 ml. of hot water, filtered and washed with hot water. The combined filtrate and wash is cooled to 5° C. and the resulting crystals are collected by filtration giving disodium 5-nitrobenzene-1,3-disulfonate.

A mixture of 163.5 g. of disodium-5-nitrobenzene-1,3-disulfonate, 502 g. of thionyl chloride and 10 ml. of dimethylformamide is refluxed overnight, cooled and chloroform is added. The mixture is filtered, washed with chloroform and the combined filtrate and washing is evaporated to a yellow solid. This solid is recrystallized by boiling in a mixture of 50 ml. of chloroform and 300 ml. of carbon tetrachloride, cooling in an ice bath and drying the solid in vacuo at 60° C. giving 5-nitro-1,3-benzenedisulfonyl chloride.

A mixture of 127 g. of 5-nitro-1,3-benzenedisulfonyl chloride, 127 g. of p-tert.-butyl phenol and 350 ml. of dry pyridine is stirred first at room temperature and then on a steam bath for 2 hours. The mixture is cooled and poured into a mixture of ice and 420 ml. of concentrated hydrochloric acid, bringing the total volume to 2 liters, and stirred for one hour. The resulting solid is collected by filtration, washed with water, dried and then dissolved in a hot mixture of 400 ml. of acetone and 450 ml. of ethanol. The mixture is cooled to room temperature and then cooled in an ice bath for 2 hours. The resulting solid is collected by filtration, washed with cold ethanol and dried at 75° C., giving 5-nitro-1,3-benzenedisulfonic acid, di-(p-tert,-butylphenyl)ester.

A mixture of 138 g. of 5-nitro-1,3-benzenedisulfonic acid, di-(p-tert.-butylphenyl)ester and 14 g. of 10% palladium on carbon catalyst in 1.2 liters of tetrahydrofuran is hydrogenated on a Parr shaker at 20 lb./sq. in. initial pressure and the temperature maintained below 40° C. for 3½ hours. A 7.0 g. portion of 10% palladium on carbon is added and hydrogenation continued for 2 hours. The catalyst is removed by filtration, 7.0 g. of fresh catalyst is added to the filtrate and hydrogenation is continued for 22 hours. The catalyst is removed by filtration. The filtrate is concentrated to dryness and the residue is crystallized from hot toluene, giving 5-amino-m-benzenedisulfonic acid, di-(p-tert.-butylphenyl)ester.

To a solution of 23.3 g. of 5-amino-m-benzenedisulfonic acid di-(p-tert.-butylphenyl)ester in 75 ml. of dry pyridine is added 6.16 g. of 1,3,5-benzenetrisulfonyl chloride. The mixture is stirred at 40°-83° C. over one hour, cooled and poured into 375 ml. of water containing 78 ml. of concentrated hydrochloric acid. The resulting solid is collected by filtration and washed with water. This solid is stirred with 500 ml. of 0.5 N sodium hydroxide for 30 minutes, then acidified with 26 ml. of concentrated hydrochloric acid, filtered and the solid is washed with water and air dried overnight. This solid is dissolved in 250 ml. of dichloromethane, giving an emulsion which is partially broken with the addition of 200 ml. of saturated aqueous sodium chloride solution. The layers are separated and the remaining emulsion is broken up by filtration through a sintered glass funnel. The combined organic layers are dried over sodium sulfate, filtered through diatomaceous silica and evaporated to a yellow glass. This glass is dissolved in 100 ml. of dichloromethane and filtered through 100 g. of hydrous magnesium silicate. The hydrous magnesium silicate is washed with 200 ml., 200 ml. and 400 ml. of dichloromethane. The individual washes are evaporated, the solids from each are combined and dried overnight in a pistol at 56° C. giving 5,5′,5″-[s-phenenyltris(sulfonylimino)]tri-m-benzenedisulfonic acid, hexa(p-tert.-butylphenyl)ester as a pale yellow glass.

A 2.0 g portion of sodium is dissolved in 50 ml. of absolute ethanol, evaporated to dryness and the residue is dissolved in 25 ml. of dimethylsulfoxide. To this is added a solution of 9.1 g. of 5,5′,5″-[s-phenenyltris(sulfonylimino)]-tri-m-benzenedisulfonic acid, hexa(p-tert.-butylphenyl)ester in 25 ml. of dimethyl sulfoxide. The solution is heated on a steam bath for 30 minutes, cooled, poured into 500 ml. of absolute ethanol to provide the N-sodio salt of the title compound which is acidified with 5 ml. of acetic acid. The resulting hexasodium compound is collected by filtration and washed with ethanol and ether. This solid is dissolved in 25 ml. of water, 1.0 g. of sodium acetate trihydrate is added and the solution is poured into 250 ml. of absolute ethanol. The resulting solid is collected by filtration, washed with ethanol and ether and dried in a pistol at 110° C. overnight, giving the desired product as a beige powder.

EXAMPLE 2

4,4′,4″-[s-Phenenyltris(sulfonylimino)]tri-benzenesulfonic acid, trisodium salt Following the procedure of Example 1, the use of sodium p-nitrobenzenesulfonie provides the product of the example.

EXAMPLE 3

Preparation of Compressed Tablet

| Ingredient | mg/Tablet |
|---|---|
| Active Compound | 0.5-500 |
| Dibasic Calcium Phosphate N.F. | qs |
| Starch USP | 40 |
| Modified Starch | 10 |
| Magnesium Stearate USP | 1-5 |

EXAMPLE 4

Preparation of Compressed Table (Sustained Action)

| Ingredient | mg/Tablet |
|---|---|
| Active Compound as Aluminum Lake*, Micronized | 0.5-500 (as acid equivalent) |
| Dibasic Calcium Phosphate N.F. | qs |
| Alginic Acid | 20 |
| Starch USP | 35 |
| Magnesium Stearate USP | 1-10 |

*Complement inhibitor plus aluminum sulfate yields aluminum complement inhibitor. Complement inhibitor content in aluminum lake ranges from 5-30°.

EXAMPLE 5

Preparation of Hard Shell Capsule

| Ingredient | mg/Capsule |
|---|---|
| Active Compound | 0.5-500 |
| Lactose, Spray Dried | qs |
| Magnesium Stearate | 1-10 |

EXAMPLE 6

Preparation of Oral Liquid (Syrup)

| Ingredient | % W/V |
|---|---|
| Active Compound | 0.05-5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 7

Preparation of Oral Liquid (Elixir)

| Ingredient | % W/V |
|---|---|
| Active Compound | 0.05-5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 8

Preparation of Oral Suspension (Syrup)

| Ingredient | % W/V |
|---|---|
| Active Compound as Aluminum Lake, Micronized | 0.05-5 (acid equivalent) |
| Polysorbate 80 USP | 0.1 |

-continued

| Ingredient | % W/V |
|---|---|
| Magnesium Aluminum Silicated, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 9

Preparation of Injectable Solution

| Ingredient | % W/V |
|---|---|
| Active Compound | 0.05-5 |
| Benzyl Alcohol N.F. | 0.9 |
| Water for Injection | 100.0 |

EXAMPLE 10

Preparation of Injectable Oil

| Ingredient | % W/V |
|---|---|
| Active Compound | 0.05-5 |
| Benzyl Alcohol | 1.5 |
| Sesame Oil qs ad | 100.0 |

EXAMPLE 11

Preparation of Intra-Articular Product

| Ingredient | Amount |
|---|---|
| Active Compound | 2-20 mg. |
| NaCl (physiological saline) | 0.9% |
| Benzyl Alcohol | 0.9% |
| Sodium Carboxymethylcellulose | 1-5% |
| pH adjusted to 5.0-7.5 | |
| Water for Injection qs ad | 100% |

EXAMPLE 12

Preparation of Injectable Depo Suspension

| Ingredient | % W/V |
|---|---|
| Active Compound | 0.05-5 (acid equivalent) |
| Polysorbate 80 USP | 0.2 |
| Polyethylene Glycol 400 USP | 3.0 |
| Sodium Chloride USP | 0.8 |
| Benzyl Alcohol N.F. | 0.9 |
| HCl to pH 6-8 | qs |
| Water for Injection qs ad | 100.0 |

EXAMPLE 13

Preparation of Dental Paste

| Ingredient | % W/V |
|---|---|
| Active Compound | 0.05-5 |
| Zinc Oxide | 15 |
| Polyethylene Glycol 4000 USP | 50 |
| Distilled Water qs | 100 |

EXAMPLE 14

Preparation of Dental Ointment

| Ingredient | % W/W |
|---|---|
| Active Compound | 0.05-5 |
| Petrolatum, White USP qs | 100 |

EXAMPLE 15

Preparation of Dental Cream

| Ingredient | % W/W |
|---|---|
| Active Compound | 0.05-5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 16

Preparation of Topical Cream

| Ingredient | % W/W |
|---|---|
| Active Compound | 0.05-5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 17

Preparation of Topical Ointment

| Ingredient | % W/W |
|---|---|
| Active Compound | 0.05-5 |
| Cholesterol | 3 |
| Stearyl Alcohol | 3 |
| White Wax | 8 |
| Petrolatum, White USP qs | 100 |

EXAMPLE 18

Preparation of Spray Lotion (non-Aerosol)

| Ingredient | % W/W |
|---|---|
| Active Compound | 0.05-5 |
| Isopropyl Myristate | 20 |
| Alcohol (Denatured) qs | 100 |

EXAMPLE 19

Preparation of Buccal Tablet

| Ingredient | g/Tablet |
|---|---|
| Active Ingredient | 0.00325 |
| 6 × Sugar | 0.29060 |
| Acacia | 0.01453 |
| Soluble Starch | 0.01453 |

-continued

| Ingredient | g/Tablet |
|---|---|
| F.D. & C. Yellow No. 6 Dye | 0.00049 |
| Magnesium Stearate | 0.00160 |
| | 0.32500 |

The final tablet will weigh about 325 mg. and may be compressed into buccal tablets in flat faced or any other tooling shape convenient for buccal administration.

EXAMPLE 20

Preparation of Lozenge

| Ingredient | g/Lozenge |
|---|---|
| Active Ingredient | 0.0140 |
| Kompact ® Sugar (Sucrest Co.) | 0.7138 |
| 6 × Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized.

We claim:

1. A method for the preparation of a compound of the formula:

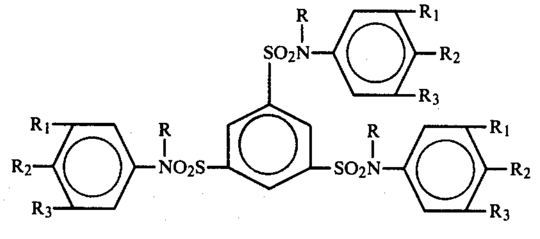

wherein each R is selected from the group consisting of hydrogen and alkali metal; each $R_1$, $R_2$, and $R_3$ is selected from the group consisting of hydrogen and $SO_3A$, wherein A is selected from the group consisting of hydrogen and a pharmaceutically acceptable salt cation; provided that at least one of the $R_1$, $R_2$, $R_3$ groups on each phenyl is $SO_3A$; and further provided that when $R_2$ is $SO_3A$, $R_1$ and $R_3$ may not be $SO_3A$; which comprises reacting 1,3,5-benzenetrisulfonyl chloride with a compound of the formula:

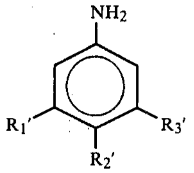

wherein $R'_1$, $R'_2$, $R'_3$ are each selected from the group consisting of hydrogen and

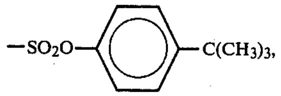 with the proviso that at least one of the $R_1'$, $R_2'$, $R_3'$ groups on the phenylamine is

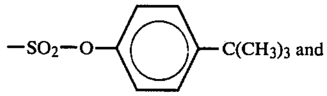 and when $R_2'$ is

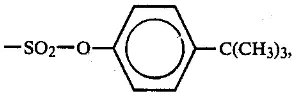 $R_1'$ and $R_3'$ may not be

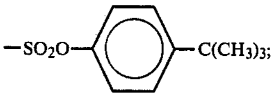

in an organic nitrogen base for over one hour; acidifying with a mineral acid; treating the resulting ester with alkali metal $C_1$–$C_6$ alkoxide in dimethylsulfoxide at an elevated temperature for about one hour; acidifying with an organic acid; reprecipitating from absolute $C_1$–$C_6$ alkanol in the presence of an alkali metal acetate to yield the alkali metal salt, and optionally displacing said alkali metal cation with another pharmaceutically acceptable salt cation.

* * * * *